United States Patent
Dooley (10) Patent No.: US 9,393,027 B1
(45) Date of Patent: Jul. 19, 2016

(54) INTRAVENOUS ASSIST DEVICE

(75) Inventor: Daniel P. Dooley, Oklahoma City, OK (US)

(73) Assignee: Frank Gleason I.P., LLC, Oklahoma City, OK (US)

( * ) Notice: Subject to any disclaimer, the term of this patent is extended or adjusted under 35 U.S.C. 154(b) by 443 days.

(21) Appl. No.: 13/565,192

(22) Filed: Aug. 2, 2012

(51) Int. Cl.
*A61B 17/00* (2006.01)
*A61B 17/132* (2006.01)

(52) U.S. Cl.
CPC ........... *A61B 17/1325* (2013.01); *A61B 17/132* (2013.01)

(58) Field of Classification Search
CPC ............. A61B 17/135; A61B 17/1355; A61B 17/132–17/1327; A61H 9/005; A61H 9/0078; A61H 9/0092
USPC ............................ 600/490–499; 606/201–203
See application file for complete search history.

(56) References Cited

U.S. PATENT DOCUMENTS

| | | | |
|---|---|---|---|
| 2,618,269 A * | 11/1952 | Baum et al. | 606/202 |
| 3,752,148 A * | 8/1973 | Schmalzbach | 600/499 |
| 3,906,937 A * | 9/1975 | Aronson | 600/493 |
| 4,469,099 A | 9/1984 | McEwen | |
| 4,479,494 A | 10/1984 | McEwen | |
| 4,605,010 A | 8/1986 | McEwen | |
| 4,770,175 A | 9/1988 | McEwen | |
| 4,869,265 A | 9/1989 | McEwen | |
| 5,048,536 A | 9/1991 | McEwen | |
| 5,181,522 A | 1/1993 | McEwen | |
| 5,254,087 A | 10/1993 | McEwen | |
| 5,312,431 A | 5/1994 | McEwen | |
| 5,352,195 A | 10/1994 | McEwen | |
| 5,439,477 A | 8/1995 | McEwen | |
| 5,454,831 A | 10/1995 | McEwen | |
| 5,556,415 A | 9/1996 | McEwen | |
| 5,578,055 A | 11/1996 | McEwen | |
| 5,584,853 A | 12/1996 | McEwen | |
| 5,607,447 A | 3/1997 | McEwen et al. | |
| 5,649,954 A | 7/1997 | McEwen | |
| 5,681,339 A | 10/1997 | McEwen et al. | |
| 5,741,295 A | 4/1998 | McEwen | |
| 5,855,589 A | 1/1999 | McEwen et al. | |
| 5,911,735 A | 6/1999 | McEwen | |
| 5,931,853 A | 8/1999 | McEwen | |
| 5,935,146 A | 8/1999 | McEwen | |
| 6,213,939 B1 | 4/2001 | McEwen | |
| 6,361,548 B1 | 3/2002 | McEwen | |
| 6,378,552 B1 * | 4/2002 | Pekar et al. | 137/512.4 |
| 6,589,268 B1 | 7/2003 | McEwen | |
| 6,682,547 B2 | 1/2004 | McEwen | |
| 6,746,470 B2 * | 6/2004 | McEwen et al. | 606/202 |
| 7,331,977 B2 | 2/2008 | McEwen et al. | |
| 7,384,425 B2 | 6/2008 | McEwen et al. | |

(Continued)

*Primary Examiner* — David C Eastwood
(74) *Attorney, Agent, or Firm* — Hall Estill Attorneys at Law; Daniel P. Dooley (57) ABSTRACT

Preferably, an intravenous assist device includes at least, a pneumatic tourniquet portion, a pneumatic barrier having a first side contactingly adjacent the pneumatic barrier, a tissue compression portion contactingly adjacent a second side of said pneumatic barrier, and a pneumatic gate in fluid communication with each the pneumatic tourniquet portion and the tissue compression portion. The pneumatic gate promotes an inflation of the tissue compression portion only after full inflation of the pneumatic tourniquet forms a tourniquet. The pneumatic gate is formed between the pneumatic tourniquet portion and the tissue compression portion by an aperture only.

14 Claims, 7 Drawing Sheets

(56) References Cited

U.S. PATENT DOCUMENTS

| | | | |
|---|---|---|---|
| 7,479,154 B2 | 1/2009 | McEwen et al. | |
| 7,758,607 B2* | 7/2010 | McEwen et al. | 606/203 |
| 7,780,698 B2* | 8/2010 | McEwen et al. | 606/203 |
| 8,137,378 B2* | 3/2012 | McEwen et al. | 606/203 |
| 8,759,603 B2* | 6/2014 | Wada et al. | 602/53 |
| 2005/0070828 A1* | 3/2005 | Hampson et al. | 601/152 |
| 2006/0224181 A1 | 10/2006 | McEwen et al. | |
| 2006/0287672 A1 | 12/2006 | McEwen et al. | |
| 2007/0032818 A1 | 2/2007 | McEwen et al. | |
| 2007/0032819 A1 | 2/2007 | McEwen et al. | |
| 2007/0135835 A1 | 6/2007 | McEwen et al. | |
| 2007/0135836 A1 | 6/2007 | McEwen et al. | |
| 2007/0219580 A1* | 9/2007 | McEwen et al. | 606/202 |
| 2007/0244506 A1 | 10/2007 | McEwen et al. | |
| 2008/0262533 A1 | 10/2008 | McEwen et al. | |
| 2010/0130877 A1* | 5/2010 | Matsumoto et al. | 600/499 |
| 2010/0268267 A1* | 10/2010 | McEwen et al. | 606/203 |
| 2012/0041476 A1* | 2/2012 | Lin | 606/202 |
| 2013/0245675 A1* | 9/2013 | Wada et al. | 606/202 |
| 2013/0282048 A1* | 10/2013 | Wada et al. | 606/202 |

\* cited by examiner

INTRAVENOUS ASSIST DEVICE

FIELD OF THE INVENTION

The present invention relates generally to the intravenous procedure device, but not by way of limitation, to the field of medical equipment.

SUMMARY OF THE INVENTION

In accordance with the exemplary embodiments, a preferred intravenous assist device includes at least a pneumatic tourniquet portion, a pneumatic barrier having a first side in contact adjacency with the pneumatic barrier, a tissue compression portion in contact adjacency with a second side of said pneumatic barrier, and a pneumatic gate in fluid communication with each the pneumatic tourniquet portion and the tissue compression portion, wherein the pneumatic gate promotes an inflation of the tissue compression portion only after full inflation of the pneumatic tourniquet forms a tourniquet, and wherein the pneumatic gate is formed between the pneumatic tourniquet portion and the tissue compression portion by an aperture only. Preferably, the intravenous assist device exemplary embodiment further includes a cover portion and a backing portion, the cover portion and the backing portion are joined one to the other by the pneumatic barrier, a seal enclosing the tourniquet portion and the tissue compression portion and further joining the cover portion to the backing portion, in which the backing portion, the cover portion, the first side of the pneumatic barrier, and the seal form the tourniquet portion, and the backing portion, the cover portion, the second side of the pneumatic barrier, and the seal form the tissue portion.

Additionally, the intravenous assist device exemplary embodiment further preferably includes an inflation conduit in fluid communication with the tourniquet portion, a pneumatic pump in fluid communication with the inflation conduit, and a fill line disposed between the pneumatic pump and the inflation conduit.

In an alternate preferred embodiment, the intravenous assist device is formed by steps that includes at least, providing a pneumatic tourniquet portion, forming a pneumatic barrier having a first side in contact adjacency with the pneumatic barrier, supplying a tissue compression portion in contact adjacency with a second side of said pneumatic barrier, and forming a pneumatic gate in fluid communication with each the pneumatic tourniquet portion and the tissue compression portion, wherein the pneumatic gate promotes an inflation of the tissue compression portion only after full inflation of the pneumatic tourniquet forms a tourniquet, and wherein the pneumatic gate is formed between the pneumatic tourniquet portion and the tissue compression portion by an aperture only.

These and various other features and advantages which characterize the claimed invention will be apparent from reading the following detailed description and a review of the associated drawings.

DETAILED DESCRIPTION OF THE INVENTION

Exemplary embodiments of the present invention are generally directed to a blood vessel access assistance device configured to facilitate a transfer of IV fluids into a predetermined blood vessel. Reference will now be made in detail to the presently exemplary embodiments of the invention, one or more examples of which are illustrated in the accompanying drawings. Each example is provided by way of explanation of the invention, not limitation of the invention. In fact, it will be apparent to those skilled in the art that various modifications and variations can be made in the present invention without departing from the scope or spirit of the invention. For example, features illustrated or described as part of one embodiment, can be used on another embodiment to yield a still further embodiment. Thus, it is intended that the present invention cover such modifications and variations as come within the scope of the appended claims and their equivalents. Additionally, the numbering of components in the drawings is consistent throughout the application, with the same components having the same number in each of the drawings.

Figure 1:
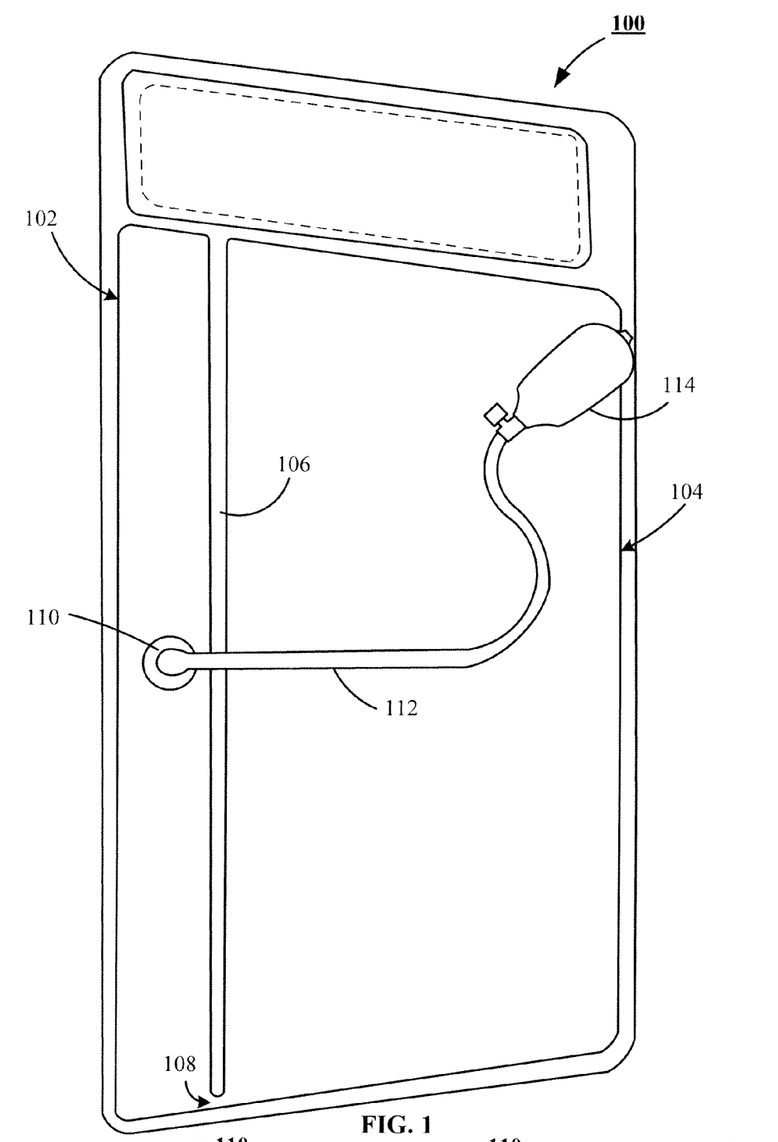
FIG. 1 is a top plan view of an exemplary embodiment of a novel intravenous assist device.

FIG. 1 shows an exemplary intravenous assist device 100 preferably includes at least a pneumatic tourniquet portion 102 formed on a proximal end of the intravenous assist device 100, a tissue compression portion 104 on a distal end of the device, a pneumatic barrier 106 disposed between the pneumatic tourniquet portion 102 and the tissue compression portion 104, and a pneumatic gate 108 formed adjacent the pneumatic barrier 106 and providing selective communication of fluid between the pneumatic tourniquet portion 102 and the tissue compression portion 104.

To facilitate an inflation of each the pneumatic tourniquet portion 102 and the tissue compression portion 104, FIG. 1 further shows the exemplary intravenous assist device 100 preferably includes an inflation conduit 110 mounted to the pneumatic tourniquet 102 with a fill line 112 attached to the inflation conduit 110. Preferably, the embodiment shown by FIG. 1 additionally shows a pneumatic pump 114 is secured to the fill line 112. As illustrated the pneumatic pump 114 is a manually operated pneumatic pump. However as those skilled in the art will recognize that a mechanically operated pneumatic pump selected from a number of known mechanically operated pneumatic pumps could be utilized for an inflation of each the pneumatic tourniquet portion 102 and the tissue compression 104 during a utilization of the exemplary intravenous assist device 100 on a patient.

Figure 2:
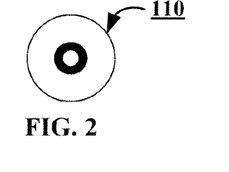
FIG. 2 is a top plan view of a fill conduit of the novel intravenous assist device of FIG. 1.
Figure 3:
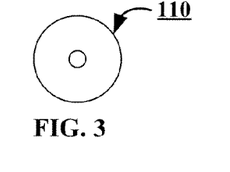
FIG. 3 is a bottom plan view of the fill conduit of FIG. 2.
Figure 4:
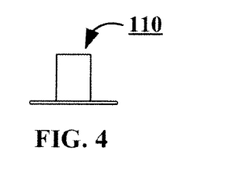
FIG. 4 is a view in elevation of the fill conduit of FIG. 2.

FIG. 2 shows a plan view of a first preferred embodiment of the inflation conduit 110, FIG. 3 depicts a bottom plan view of the first preferred embodiment of the inflation conduit 110, while FIG. 4 illustrates a view in elevation of the first preferred inflation conduit 110.

Figure 5:
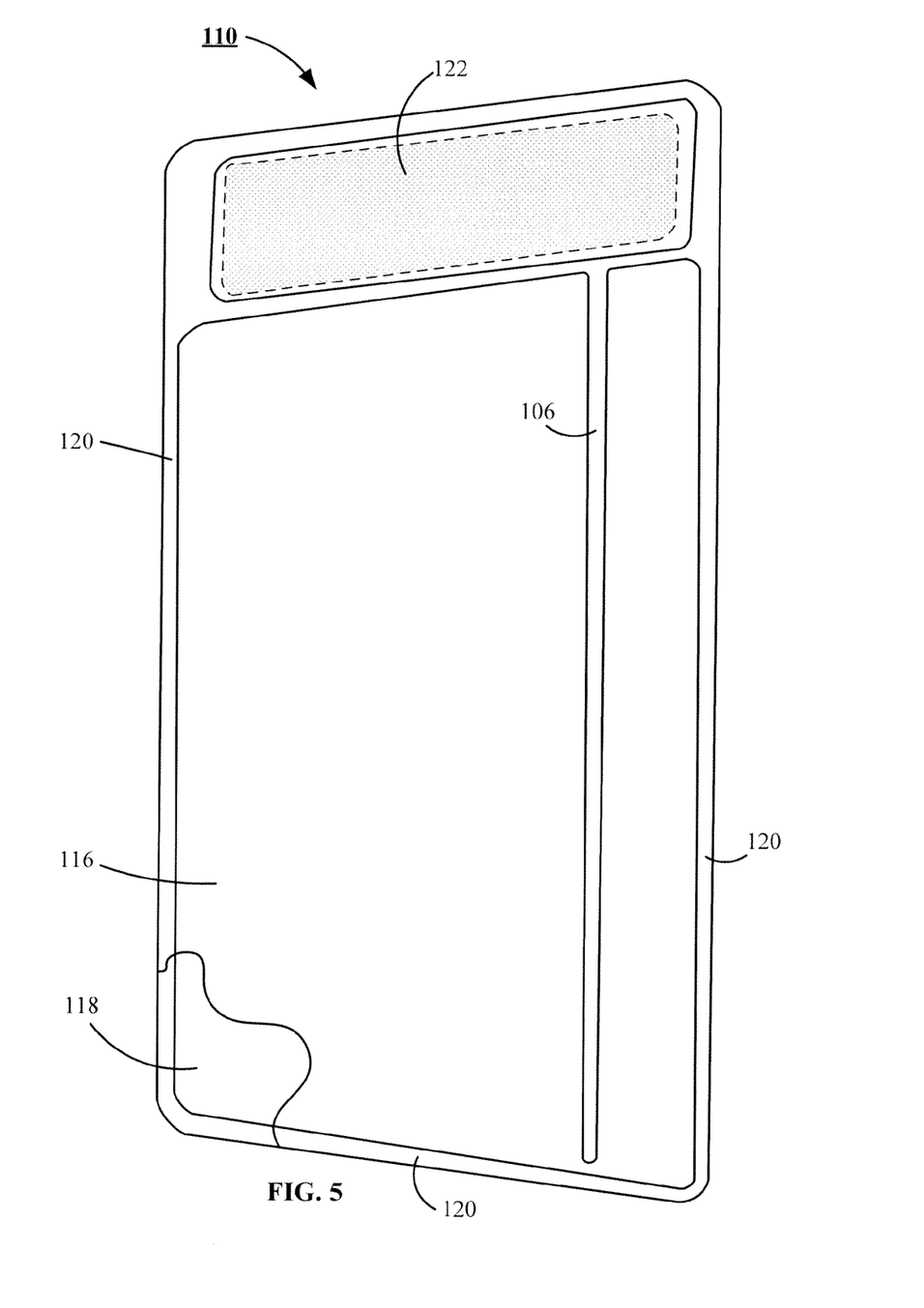
FIG. 5 is a partial cutaway bottom plan view of the exemplary embodiment of the novel intravenous assist device of FIG. 1.

The bottom plan view of the exemplary intravenous assist device 100 shown by FIG. 5, reveals that a backing portion 116 is secured to a cover portion 118 by a seal 120, which surrounds pneumatic tourniquet portion 102, the tissue compression portion 104, the pneumatic barrier 106, and the pneumatic gate 108 to form the intravenous assist device 100. FIG. 5 also shows a preferred embodiment of the intravenous assist device 100 includes a retention member 122 secured to the backing portion 116.

Figures 6, 7, 8, 9:
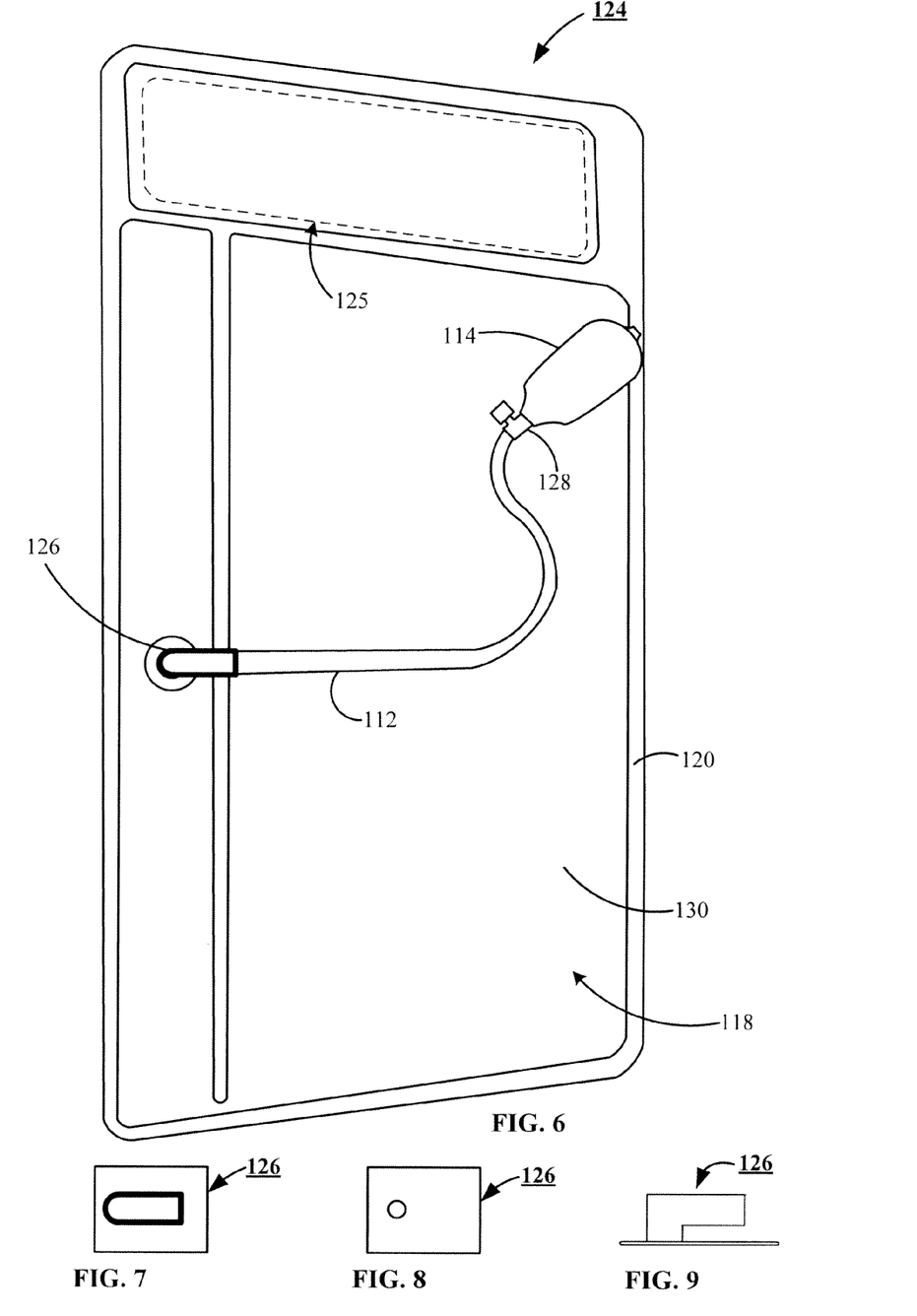
FIG. 6 is a top plan view of an alternate exemplary embodiment of the novel intravenous assist device.
FIG. 7 is a top plan view of an alternate fill conduit of the novel intravenous assist device of FIG. 6.
FIG. 8 is a bottom plan view of the alternate fill conduit of FIG. 7.
FIG. 9 is a view in elevation of the alternate fill conduit of FIG. 7.

FIG. 6 shows an alternate preferred embodiment of the intravenous assist device 124 that includes an alternate inflation conduit 126, that the retention number 122 of FIG. 5 is preferably sewn to the intravenous assist device 100 by stitches 125, and that the pneumatic pump 114 further provides a control valve 128. In a preferred embodiment, the cover portion 118 provides a securement feature 130 in the form of a loop portion of a hook and loop system, while the retention member 122 provides the hook portion of the hook and loop system such that when the intravenous assist device 100 is utilized with a patient, the hook portion of the hook and loop system interacts with the loop portion of the hook and loop system to secure the intravenous assist device 100 to the patient.

FIG. 7 shows a plan view of a second preferred embodiment of the inflation conduit 126, FIG. 8 depicts a bottom plan view of the second preferred embodiment of the inflation conduit 126, while FIG. 9 illustrates a view in elevation of the second preferred inflation conduit 126.

Figure 10:
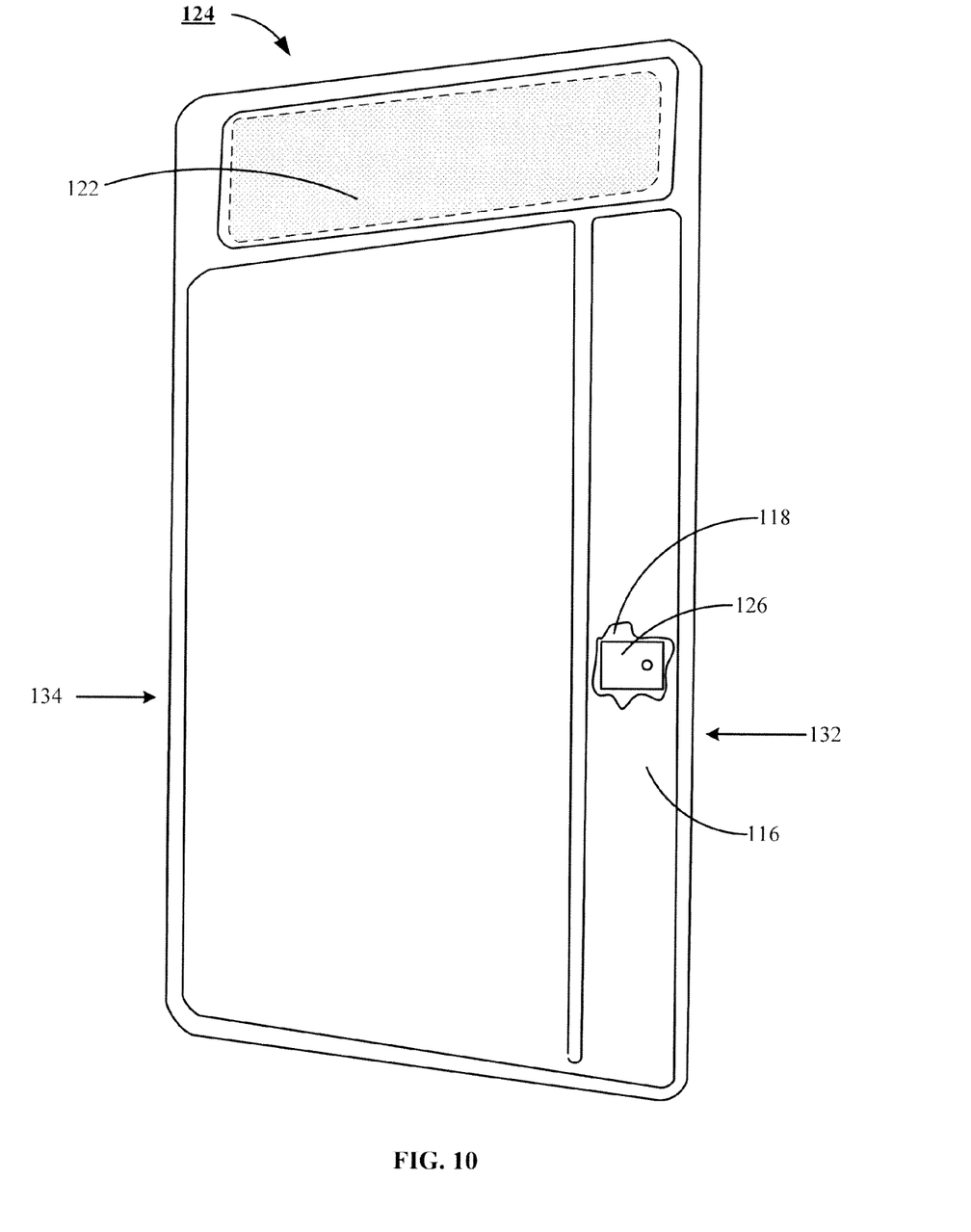
FIG. 10 is a partial cutaway bottom plan view of the alternate exemplary embodiment of the novel intravenous assist device of FIG. 6.
Figure 11:
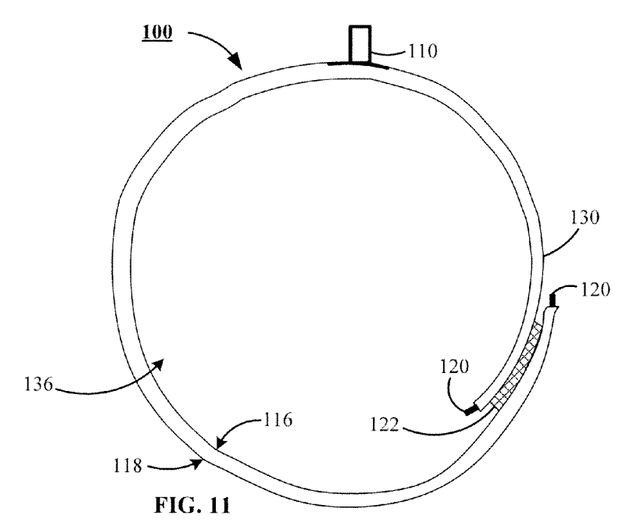
FIG. 11 is an end view in cross section of a non-inflated exemplary embodiment of the novel intravenous assist device of FIG. 1.
Figure 12:
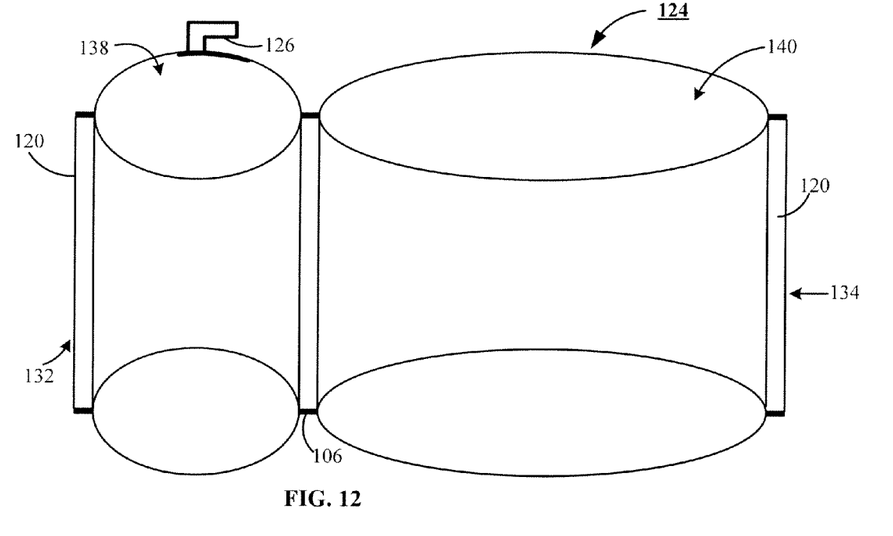
FIG. 12 is a cross section view in elevation of the exemplary embodiment of the novel intravenous assist device of FIG. 1.

FIG. 10 illustrates the inflation conduit 126 in secured to the cover portion 118 and adjacent a proximal end 132 of the intravenous assist device 124, the retention portion 122 (the hook portion of the hook and system) secured to the backing portion 116 and disposed between the proximal end 132 and a distal end 134 of the intravenous assist device 124. FIG. 11 shows in cross section, the intravenous assist device 100 in a non-inflated state, wrapped about a limb of a patient 136 with the retention member 122 secured to the securement feature 130. FIG. 12 shows in cross section, the intravenous assist device 100 in an inflated state, which in an inflated state and secured to a limb of the patient 136 of FIG. 5, forms each a tourniquet 138 and a compression cuff 140. In a preferred embodiment, shown by FIG. 5, an internal volume of the tourniquet 138 is less than internal volume of the compression cuff 140.

Figure 13:
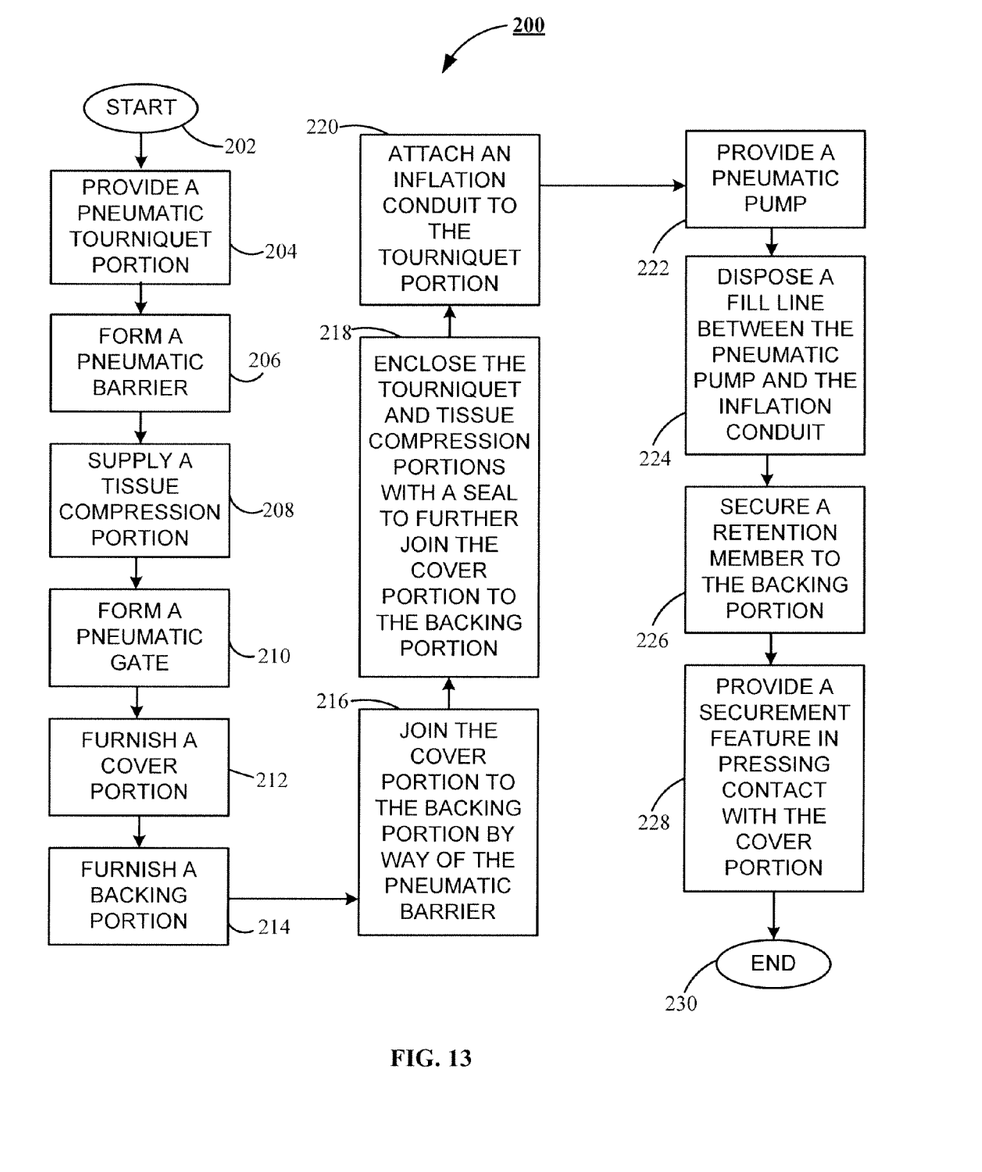
FIG. 13 is a flow chart of a method of making an embodiment of the novel intravenous assist device of FIGS. 1 and 6.

FIG. 13 shows a flow chart of a method of making an embodiment of the inventive intravenous assist device 200 (such as 100 and 124) beginning and start step 202 and continuing at process step 204. At process step 204, a pneumatic tourniquet portion (such as 102) is provided, and at process step 206 a pneumatic barrier (such as 106) is formed. At process step 208, a tissue compression portion (such as 104) is supplied, and at process step 210, a pneumatic gate (such as 108) is formed.

At process step 212, a cover portion (such as 118) is furnished and at process step 214, a backing portion (such as 116) is furnished. At process step 216, the cover portion is joined to the backing portion by way of the pneumatic barrier, and at process 218, the tourniquet portion and a tissue compression portion are enclosed by a seal (such as 120), which further serves to join the cover portion to the backing portion. At process step 220, and inflation conduit (such as 110 and 126) is attached to the tourniquet portion of the intravenous assist device.

At process step 222, a pneumatic pump (such as 114) is provided, and at process step 224, a fill line (such as 112) is disposed between and connected to the pneumatic pump and the inflation conduit. At process step 226, a retention member (such as 122) is secured to the backing portion, and at process step 228, a secure feature (such as 130) is provided by the cover portion. Preferably, the combination of the front portion, back portion, pneumatic barrier, pneumatic gate, and seal joined to form each the tourniquet portion and the adjacent tissue compression portion.

Figure 14:
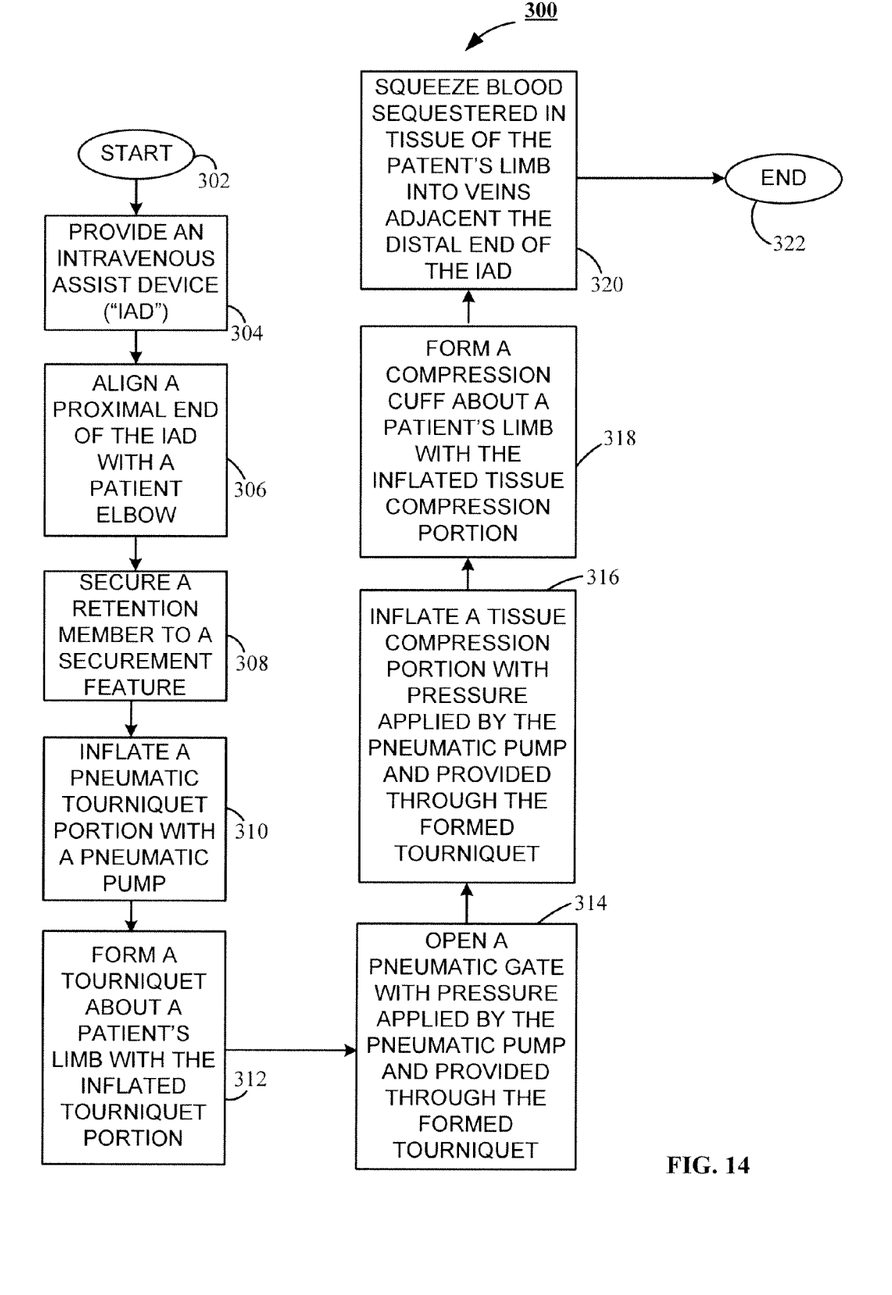
FIG. 14 is a flow chart of a method of using an embodiment of the novel intravenous assist device of FIGS. 1 and 6.

FIG. 14 is a flowchart of a method 300 of using an inventive intravenous assist device (such as 100, 124), commencing at start step 302 and continuing to process step 304. At process step 304, the intravenous assist devices provide. At process step 306, a proximal end (such as 132) is aligned adjacent a joint (such as an elbow) of a patient (such as 136), and wrapped about the patient's limb. At process step 308, a retention member (such as 122) is secured to a securement feature (such as 130), in preparation for an inflation of the tourniquet portion, which forms a tourniquet (such as 138), and an inflation of the tissue compression portion, which forms a compression cuff (such as 140).

At process step 310, a pneumatic pump (such as 114) is used to commence inflation of the pneumatic tourniquet portion, and at process step 312, with the intravenous assist device wrapped about insecure to enclose a limb of the patient, the tourniquet is formed through continued inflation of the pneumatic tourniquet portion using the pneumatic pump. With the tourniquet fully formed and continued activation of the pneumatic pump, a pneumatic gate (such as 108) is opened between the fully formed tourniquet and the tissue compression portion of the intravenous assist device at process step 314. At process step 316, through continued activation of the pneumatic pump, a fluid is pumped through the fully formed tourniquet and into the tissue compression portion of the intravenous assist device.

At process step 318, with continued activation of the pneumatic pump, the compression portion is formed, which as shown by process step 320, squeezes blood sequestered in the tissue of the patient's limb into veins adjacent a distal end (such as 134) of the intravenous assist device, and the process concludes at end process step 322.

It will be clear that the present invention is well adapted to attain the ends and advantages mentioned as well as those inherent therein. While presently exemplary embodiments have been described for purposes of this disclosure, numerous changes may be made which will readily suggest themselves to those skilled in the art and which are encompassed by the appended claims.

What is claimed is:

1. An apparatus comprising:
   a single chamber pneumatic tourniquet having a length and a width, the single chamber pneumatic tourniquet length greater than the single chamber pneumatic tourniquet width;
   a pneumatic barrier having a first side in contact adjacency with the single chamber pneumatic tourniquet;
   a single chamber tissue compression member in contact adjacency with a second side of said pneumatic barrier, the single chamber tissue compression member having a length and a width, the single chamber tissue compression member length greater than the single chamber pneumatic tissue compression member width, the single chamber tissue compression member running substantially parallel to the single chamber pneumatic tourniquet along its entire length, the single chamber pneumatic tourniquet configured for surrounding substantially an entirety of a limb of a patient and in which the apparatus includes two and only two chambers, the single chamber pneumatic tourniquet and the single chamber tissue compression member; and a pneumatic gate in fluid communication with each of the single chamber pneumatic tourniquet and the single chamber tissue compression member, wherein the pneumatic gate promotes an inflation of the tissue compression member only after full inflation of the single chamber pneumatic tourniquet forms a tourniquet, where in the tourniquet precludes return blood flow through the patient's veins below the formed tourniquet, prior to inflation of the single chamber tissue compression portion, and wherein the pneumatic gate is formed between the single chamber pneumatic tourniquet and the single chamber tissue compression member by an aperture only, and further wherein the width of the single chamber pneumatic tourniquet is less than the width of the single chamber tissue compression member such that an internal volume of the single chamber pneumatic tourniquet is less than an internal volume of the single chamber tissue compression member.

2. The apparatus of claim 1, further comprising a cover portion and a backing portion, the cover portion and the backing portion joined one to the other by the pneumatic barrier.

3. The apparatus of claim 2, further comprising a seal enclosing the single chamber tourniquet and the single chamber tissue compression member and further joining the cover portion to the backing portion.

4. The apparatus of claim 3, in which the backing portion, the cover portion, the first side of the pneumatic barrier, and the seal form the single chamber tourniquet.

5. The apparatus of claim 4, in which the backing portion, the cover portion, the second side of the pneumatic barrier, and the seal form the single chamber tissue compression member.

6. The apparatus of claim 5, further comprising a single and only inflation conduit in fluid communication with the single chamber pneumatic tourniquet.

7. The apparatus of claim 6, further comprising a single and only pneumatic pump in fluid communication with the inflation conduit, and a single and only fill line disposed between the pneumatic pump and the inflation conduit.

8. The apparatus of claim 2, further comprising a retention member secured to the backing portion.

9. The apparatus of claim 8, in which the cover portion provides a securement feature.

10. The apparatus of claim 9, in which the retention member is a hook portion of a hook and loop fastening system, and the securement feature is a loop portion of the hook and loop fastening system.

11. The apparatus of claim 10, in which the tourniquet is formed when the backing portion surrounds a limb of a patient, the hook portion interacts with the loop portion to secure the backing portion in contact adjacency with the patient's limb, the pneumatic pump is activated to inflate the single chamber tourniquet.

12. The apparatus of claim 7, further comprising a compression cuff formed when the tourniquet is formed and the pneumatic pump is further activated forcing fluid through the pneumatic gate to inflate the single chamber tissue compression member, thereby squeezing blood sequestered in the tissue in the patient's limb into the patient's veins below the formed compression cuff.

13. The apparatus of claim 12, wherein following pneumatic pump activation the tissue compression member is configured to promote engorgement of the patient's veins even in the absence of a pulse of the patient.

14. A method by steps comprising:

providing a single chamber pneumatic tourniquet having a length and a width, the single chamber pneumatic tourniquet length greater than the single chamber pneumatic tourniquet width;

forming a pneumatic barrier having a first side in contact adjacency with the single chamber pneumatic tourniquet;

supplying a single chamber tissue compression member in contact adjacency with a second side of said pneumatic barrier, the single chamber tissue compression member having a length and a width, the single chamber tissue compression member length greater than the single chamber pneumatic tissue compression member width, the single chamber tissue compression member running substantially parallel to the single chamber pneumatic tourniquet along its entire length, the single chamber pneumatic tourniquet configured for surrounding substantially an entirety of a limb of a patient, and in which the apparatus includes two and only two chamber portions, the single chamber pneumatic tourniquet portion and the single chamber tissue compression portion; and forming a pneumatic gate in fluid communication with each, the single chamber pneumatic tourniquet and the single chamber tissue compression member, wherein the pneumatic gate promotes an inflation of the single chamber tissue compression member only after full inflation of the single chamber pneumatic tourniquet forms a tourniquet, where in the tourniquet precludes return blood flow through the patient's veins below the formed tourniquet prior to inflation of the single chamber tissue compression member, and wherein the pneumatic gate is formed between the single chamber pneumatic tourniquet and the single chamber tissue compression member by an aperture only, and further wherein the width of the single chamber pneumatic tourniquet is less than the width of the single chamber tissue compression member such that an internal volume of the single chamber pneumatic tourniquet is less than an internal volume of the single chamber tissue compression member.

* * * * *